(12) United States Patent
Borodic

(10) Patent No.: US 7,670,608 B2
(45) Date of Patent: Mar. 2, 2010

(54) SELECTION OF PATIENTS WITH INCREASED RESPONSIVENESS TO BOTULINUM TOXIN

(75) Inventor: Gary Borodic, Canton, MA (US)

(73) Assignee: Botulinum Toxin Research Associates, Inc., Quincy, MA (US)

( * ) Notice: Subject to any disclaimer, the term of this patent is extended or adjusted under 35 U.S.C. 154(b) by 0 days.

(21) Appl. No.: 10/793,740

(22) Filed: Mar. 8, 2004

(65) Prior Publication Data

US 2004/0175390 A1    Sep. 9, 2004

Related U.S. Application Data

(60) Provisional application No. 60/453,040, filed on Mar. 6, 2003.

(51) Int. Cl.
*A61K 39/00* (2006.01)
*A61K 39/38* (2006.01)

(52) U.S. Cl. ............. 424/239.1; 424/184.1; 424/234.1; 424/247.1; 424/236.1; 514/2; 514/8

(58) Field of Classification Search ............. 424/184.1, 424/239.1, 252.33, 254.2, 50, 247.1, 236.1, 424/94.67; 530/350; 514/2, 12, 21, 46, 47, 514/14

See application file for complete search history.

(56) References Cited

U.S. PATENT DOCUMENTS

| | | | | |
|---|---|---|---|---|
| 5,658,955 | A * | 8/1997 | Hitzig | 514/654 |
| 5,670,484 | A * | 9/1997 | Binder | 514/14 |
| 5,714,468 | A * | 2/1998 | Binder | 514/14 |
| 5,766,605 | A * | 6/1998 | Sanders et al. | 424/239.1 |
| 6,063,768 | A * | 5/2000 | First | 514/14 |
| 6,306,403 | B1 * | 10/2001 | Donovan | 424/239.1 |
| 6,328,977 | B1 * | 12/2001 | Donovan | 424/239.1 |
| 6,429,189 | B1 * | 8/2002 | Borodic | 514/2 |
| 6,447,787 | B1 * | 9/2002 | Gassner et al. | 424/247.1 |
| 6,464,986 | B1 * | 10/2002 | Aoki et al. | 424/239.1 |
| 6,623,742 | B2 * | 9/2003 | Voet | 424/236.1 |
| 6,787,517 | B1 * | 9/2004 | Gil et al. | 514/1 |
| 7,211,261 | B1 * | 5/2007 | Moyer et al. | 424/236.1 |
| 7,494,661 | B2 * | 2/2009 | Sanders | 424/239.1 |
| 7,537,773 | B1 * | 5/2009 | Borodic | 424/282.1 |
| 2002/0187164 | A1 * | 12/2002 | Borodic | 424/247.1 |
| 2002/0192239 | A1 * | 12/2002 | Borodic et al. | 424/247.1 |
| 2004/0138097 | A1 * | 7/2004 | Guyuron | 514/2 |
| 2004/0151741 | A1 * | 8/2004 | Borodic | 424/239.1 |
| 2004/0167223 | A1 * | 8/2004 | Popp | 514/568 |
| 2004/0247606 | A1 * | 12/2004 | Borodic et al. | 424/184.1 |
| 2004/0248188 | A1 * | 12/2004 | Sanders | 435/7.1 |
| 2005/0214217 | A1 * | 9/2005 | Levite | 424/9.1 |
| 2006/0182767 | A1 * | 8/2006 | Borodic | 424/239.1 |
| 2007/0148189 | A1 * | 6/2007 | Moyer et al. | 424/239.1 |

OTHER PUBLICATIONS

Velickovic, M et al, Drugs, 2001, vol. 61(13), pp. 1921-1943, Cervical Dystonia.*
Dayan, Steven H et al, Facial Plast. Surg. Clin. N. Am, vol. 11, pp. 349-358, 2003, Evaluation of the patient for cosmetic Botox injections.*
Velickovic et al (reference of record).*
Borodic, GE et al, pp. 1531-1544, Expert Opinion Investigational Drugs (2001), vol. 10(8), Botulinum toxin therapy for pain and inflammatory disorders: mechanisms and therapeutic effects.*
Pearce, L. Bruce et al, Toxicon, vol. 35(9), pp. 1373-1412, 1997, Pharmacologic characterization of botulinum toxin for basic science and medicine.*
Kolbasnik, Jeff et al, The American Journal of Gastroenterology, vol. 94(12), 1999, pp. 3434-3439.*
Becker-Wegerich, P et al, Clinical and Experimental Dermatology, vol. 26, pp. 619-630, pp. 619-630, Botulinum toxin a in the therapy of mimic facial lines.*
Birklein, Frank et al, Ann. Neurol., 2002, vol. 52, pp. 68-73, Sudomotor testing predicts the presence of neutralizing botulinum A toxin antibodies.*
Jankovic, J et al, Arch. Neurol., 1991, December, vol. 48(12), pp. 1253-1256, Clinical correlates of response to botulinum toxin injections.*
Borodic (2001) reference of record.*
Borodic et al (2001, reference of record).*
Dixon, Hamilton S, Otolaryngology-Head and Neck Surgery, vol. 123, pp. 48-54, 2000.*
Binder, William J. et al, Otolaryngology-Head and Neck Surgery, Dec. 2000, vol. 123(6), pp. 669-676.*

(Continued)

*Primary Examiner*—Robert B Mondesi
*Assistant Examiner*—Ginny Portner
(74) *Attorney, Agent, or Firm*—Milbank, Tweed, Hadley & McCloy LLP

(57) ABSTRACT

Botulinum toxin has been shown to be useful for the treatment of pain when administered for cervical dystonia. Given efficacy for pain relief in regional dystonia, further expanded applications have included myofascial pain, muscle tension headaches, and other forms of headache syndromes. The application in headache practice has expanded to migraine as well as certain secondary headache syndromes. Although multiple case reports involving the use of botulinum toxin have shown promise in its utility for the treatment of primary pain syndromes, to date, controlled trials have failed to consistently and more definitively prove utility. Described herein is a method for selection of patients with headache syndromes more likely to respond to botulinum administration. The method involves identifying coincident diseases and signs within the patient's medical history, and selecting such patients for induction into clinical studies for pain or preferential primary treatment of pain using a botulinum based pharmaceutical.

10 Claims, No Drawings

OTHER PUBLICATIONS

Binder, William J. et al, Disease-a-Month, 2002, vol. 48, pp. 323-335, Botulinum toxin type A(Botox) for treatment of Migraine.*

Borodic et al "Botulinum toxin for the treatment of chronic facial," Am. J. Pain. 3(1) 21-27, 2002.

Acquadro et al "Treatment of myfascial pain with botulinum toxin," Anesthesiology 80*3): 705-706, 1994.

Wheeler et al "A randomized, double-blind, prospective pilot study of botulinum toxin injection for refractory, unilateral, cervicothoracic, paraspinal, myofascial pain syndrome," Spine 23(15): 1662-6, 1998.

Silberstein et al "Botulinum toxin type A as a migraine preventive treatment," Headache 40(6): 445-50, 2000.

Borodic et al Botulinum toxin therapy for pain and inflammatory disorders: mechanisms and therapeutic effects,: XP-008005178, Expert Opinion, 10(8) 1531-1544, 2001.

Giladi Nir "The mechanism of action of Botulinum toxin type A in focal dystonia is most probably through its dual effect on efferent (motor) and afferent pathways at the injected site," XP-002286557, Journal of the Neurological Sciences, vol. 152, 2:132-1355, 1997.

* cited by examiner

SELECTION OF PATIENTS WITH INCREASED RESPONSIVENESS TO BOTULINUM TOXIN

This application claims benefit to U.S. Provisional Application Ser. No. 60/453,040 that was filed on Mar. 6, 2003.

TECHNICAL FIELD OF THE INVENTION

This invention relates to methods for identifying subjects with an increased responsiveness to the treatment of pain with botulinum toxin.

BACKGROUND OF THE INVENTION

The present inventors have surprisingly and unexpectedly discovered criteria for the selection of subjects for the treatment of pain syndromes with botulinum toxin. The present invention provides methods for identifying subjects with an increased responsiveness to the treatment of pain with botulinum toxin. Specifically, the inventors have discovered that atopic disease is associated with various pain syndromes, and the presence of atopic disease and relief of pain by tactile stimulation, geste antagoniste phenomenon, seem to have predictive value in forecasting pain response to botulinum toxin.

Botulinum neurotoxin, a toxin isolated from a strain of *Clostridium botulinum*, a deadly toxin at higher concentrations and quantities, has been used as a valuable therapeutic for the treatment of many neuromuscular diseases (e.g., dystonia, hemifacial spasm, bruxism, spasticity, cerebral palsy, torticollis), as well as sensory disorders and cutaneous disorders (myofacial pain, migraine, tension headaches, neuropathy, hyperhydrosis).

In 1983, the use of botulinum toxin was further expanded to use in cervical muscles for the adult onset spasmodic torticollis, a regional movement disease involving involuntary contraction and excessive tone within the neck. The involuntary contractions and tone result in abnormalities of head posture, involuntary tremors and head movement, hypertrophies and visibly disfigured cervical muscles, decreased range of motion of the cervical spine, and cervical and head pain. The injection of botulinum toxin to the cervical musculature proved effective for the treatment of this condition with respect to all components of the spasmodic torticollis syndrome, especially the pain component. Chi-square analysis demonstrated that pain relief (approximately 95%) was statistically greater than benefits achieved for other components of the syndrome (60-70%). Such observations lead to the proposition that botulinum toxin injections could be used to treat other myofascial pain syndromes of the head and neck. (Borodic and Acquadro (2002) Botulinum toxin for the treatment of chronic facial. *Am. J. Pain.* 3(1): 21-27; Acquadro and Borodic (1994) Treatment of myofascial pain with botulinum toxin. *Anesthesiology* 80(3): 705-706).

The application of botulinum toxin for the treatment of myofacial pain initially included tension headaches, bruxism, temporal mandibular joint syndrome, lower-back pain, and post-surgical pain after cervical surgical incisions for the treatment of acoustic neuroma (posterior fossa brain tumor). Application of botulinum toxin for the treatment of migraine headaches became popular after the coincident observation that migraine headaches were relieved after the of botulinum toxin to efface facial wrinkles on the forehead.

Multiple case reports suggest that botulinum toxin is effective for the treatment of tension and migraine headaches, as well as forms of myofacial pain syndrome. Despite this suggestion, controlled trials using small numbers of patients in the study groups, have failed to demonstrate the efficacy of botulinum toxin for the treatment of myofascial and other forms of pain. (Wheeler et al. (1998) A randomized, double-blind, prospective pilot study of botulinum toxin injection for refractory, unilateral, cervicothoracic, paraspinal, myofascial pain syndrome. *Spine* 23(15): 1662-6). The ineffectiveness of botulinum toxin to treat a variety of pain syndromes, in controlled trial, has been attributed to small sample size and relatively low statistical power. The need for larger numbers of patients and further multi-center investigations have been deemed necessary to provide stronger evidence of effectiveness.

In view of case reports suggesting that botulinum toxin is indeed effective for the treatment of migraine-headache-pain syndromes, efforts were made to conduct larger-scale studies. In an initial multi-center controlled study sponsored by the Allergan Pharmaceutical Company, one of the largest suppliers of botulinum toxin A (BOTOX-™), efficacy of botulinum toxin to prevent the repetitive occurrence of common migraine headaches (as defined by the International Headache Classification-1988) was suggested. The statistical significance of these results, however, was uncertain, inconsistent between treatment groups, and exhibited unexplained inverted dose response curves. (Silberstein et al. (2000) Botulinum toxin type A as a migraine preventive treatment. *Headache* 40(6): 445-50).

No further or additional statistically-high-powered studies of the effectiveness of botulinum toxin for the treatment of pain have emerged. This lack of new efficacy studies suggests the difficulty associated with establishing the utility of botulinum toxin for the treatment of migraine, tension, and essential primary headaches. Furthermore, physician-to-physician communications have suggested that botulinum toxin efficacy has not been demonstrated in repeated controlled-trial studies for the migraine indication.

Migraine, tension headaches, myofascial pain of the head, and chronic atypical facial headaches are representative of primary-headache disorders (headaches not associated with structural pathology within the head or not secondary to another disease process). Treatment of these conditions is associated with very high placebo response rates (up to 35%), requiring large numbers of patients to detect significant differences in clinical trials between study and control groups. Utilization of selection criteria (study-induction criteria) that identify a more responsive patient population increases the response rate for subjects within treatment groups of controlled studies, which, in turn, allows a smaller test sample to establish therapeutic efficacy in controlled trials. More importantly, selection criteria (diagnostic criteria) are the basis for accurate and effective medical therapy for any condition. Parameters which identify patients more likely to respond to a given treatment allow: 1) prioritization among therapies when multiple therapeutic options exist; 2) avoidance of therapy unlikely to be successful; and 3) facilitation of informed consent from patients considering risks and benefit ratios. Effective selection criteria assist researchers to further understand mechanisms of action based on clinical evidence.

The present invention provides methods of selecting patients suffering from various pain syndromes, including, but not limited to, myofascial pain, muscle tension headache, and chronic post operative wound syndromes, based on retrospective and prospective analysis in the application of botulinum toxin for the treatment of pain syndromes involving the head and neck.

SUMMARY OF THE INVENTION

The present invention provides methods of selecting a subject for the treatment of pain with botulinum toxin, comprising the step of identifying a subject suffering from a pain syndrome and atopic disease, wherein the identification of a subject with a pain syndrome and atopic disease is predictive of increased responsiveness to the treatment of pain with botulinum toxin. In a preferred embodiment, the pain syndrome is any one or a combination of the pain syndromes selected from the group consisting of: myofacial pain; migraine headache; post operative would pain; sinusitis-related headaches; muscle tension headaches; post-traumatic headaches; cluster headaches; temporal mandibular joint syndrome; fibromyalgia; atypical facial pain; post incisional wound pain; cervical radiculopathy; and whiplash.

In another embodiment of the present invention, subjects suffering from an atopic disease were identified by determining that a subject has a medical history of one or more of the atopic diseases selected from the group consisting of: recurrent hayfever, recurrent eczema, or asthma. In a preferred embodiment, the atopic disease is not temporarily related to the presence of pain.

The present invention also provides methods of identifying a subject with increased responsiveness to treating a pain disorder with botulinum toxin, comprising the step of screening a population of subjects to identify those subjects that suffer from a pain disorder and atopic disease, wherein the identification of a subject with a pain syndrome and atopic disease is predictive of increased responsiveness to the treatment of pain with botulinum toxin. In a preferred embodiment, the pain syndrome is any one or a combination of the pain syndromes selected from the group consisting of: myofacial pain; migraine headache; post operative would pain; sinusitis-related headaches; muscle tension headaches; post-traumatic headaches; cluster headaches; temporal mandibular joint syndrome; fibromyalgia; atypical facial pain; post incisional wound pain; cervical radiculopathy; and whiplash.

In another embodiment of the present invention, subjects suffering from an atopic disease were identified by determining that a subject has a medical history of one or more of the atopic diseases selected from the group consisting of: recurrent hayfever, recurrent eczema, or asthma. In a preferred embodiment, the atopic disease is not temporarily related to the presence of pain.

The present invention provides a method that comprises the steps of identifying or diagnosing a pain syndrome; diagnosing or eliciting a history of atopic disease; and classifying the identified pain syndrome as one with increased responsiveness to treatment with botulinum toxin. In one embodiment, a pain syndrome is identified according to the International Headache Classification System (The International Headache Society (I.H.S.)). In another embodiment, the presence or history of atopic disease is identified by eliciting a history or diagnosis of: asthma; bronchospastic symptoms; wheezing; aspirin-induced asthma; eczema; chronic-recurrent urticaria; seasonal rhinitis; recurrent atopic conjunctivitis; laryngeal edema; chronic pruritus; recurrent sinus infections associated with asthma; the presence of allergic nasal polyps or nasal mucosa; allergic edema; or multiple skin allergies on skin antigen panels. In yet another embodiment, a pain syndrome is classified as one with increased responsiveness to botulinum toxin by recommendation, advertisement, construction of investigational protocol, or package information.

The present invention also provides methods of selecting a subject for the treatment of pain with botulinum toxin, comprising the step of identifying a subject suffering from a pain syndrome that exhibits geste antagoniste phenomenon, wherein the identification of a subject with a pain syndrome that exhibits geste antagoniste phenomenon is predictive of increased responsiveness to the treatment of pain with botulinum toxin.

The methods of the present invention may be practiced with various botulinum toxin immunotypes. In one embodiment, the botulinum toxin is any one or more botulinum toxin immunotypes selected from the group consisting of: A; B; C; D; E; F; and G. Furthermore, the methods of the present invention may utilize compositions of botulinum toxin wherein the composition is administered at a dose between 0.5 and 50,000 mouse $LD_{50}$ units of botulinum toxin.

DETAILED DESCRIPTION OF THE INVENTION

A. Definitions.

As used herein, "Botulinum toxin" means a protein toxin and its complexes isolated from strains of *Clostridium botulinum*, including various immunotypes such as A, B, C1, C2, C3, D, E, F and G.

As used herein, "increased responsiveness" refers to an increase in the ratio of subjects responsive to pain treatment with botulinum toxin to total subjects (responsive and unresponsive to botulinum toxin).

As used herein, "response ratio" refers to the ratio of subjects responsive to pain treatment with botulinum toxin to total subjects (responsive and unresponsive to botulinum toxin).

As used herein, the term "screening a population" means a retrospective review and analysis of the medical history of a subject or an identification of a specific contemporaneous diagnosis.

B. Atopic Disease and Geste Antagoniste Phenomenon

The discovery that a coincidence of atopic disease and/or geste antagoniste with various pain syndromes appears related to the physiologic instability of endothelial, mast-cell, and sensory-nerve secretions. Tactile responses of mast cells to rubbing, and participation of mast cells in the sensory-nerve-adaptation process, have been noted on sensitized-mammalian conjunctiva. The atopic triad (eczema, asthma, and hayfever) identifies those individuals with genetic defects in the sensory-nerve adaptation mechanism and instability of mast cell and sensory-nerve-tip secretions (autocoids).

Atopic disease is a hereditary condition with complex genetics and abnormal immunological responses. Although there is currently no single laboratory test for the diagnosis of atopic dermatitis and related conditions, there has been substantial progress in the past decade toward understanding the basis of the immune response in allergic diseases. Asthma, allergic rhinitis, and atopic dermatitis generate allergen-specific IgE responses and tissue-specific inflammation, characterized by the local infiltration of memory T cells, eosinophils, mast cells and monocyte/macrophages. Recent studies have demonstrated that T cells infiltrating the acutely inflamed tissues of patients with atopic dermatitis, asthma, and allergic rhinitis primarily express IL-4, IL-5, and IL-13. These cytokines are thought to play a critical role in allergic responses, with the involvement of IL-4 and IL-13 in immunoglobulin isotype switching of IgE synthesis and vascular endothelial activation. IL-5 has been implicated in the enhancement of eosinophil-mediated and mast-cell mediated responses.

Mast-cell activation can also occur in the form of non-allergic mechanical stimulation in predisposed individuals (dermatographism), exercised mediated stimulation (cholinergic urticaria), and tactile responses (pressure urticaria). Mast cells have been implicated in sensory nerve up-regulation in pain, as well as release of allergic-inflammatory autocoids, such as histamine, substance P, nitric oxide, serotonin, platelet activating factor, and bradykinin, as well as other autocoids (Borodic et al. (2001) Botulinum toxin for the treatment of pain and inflammation. *Expert Opin. Investig. Drugs* 10(8):1531-1544).

Atopic dermatitis, eczema, allergic rhinitis, and asthma are all associated with mast-cell proliferation and instability. In the case of myofacial pain and chronic wound pain, the associated high incidence of atopic background appears to lend the patients more responsive to botulinum toxin. The mechanism by which pain is relieved by botulinum toxins may relate to blockage of sensitizing autocoids from mast cells. Geste antagoniste may also cause an alteration of mast-cell release, causing low quantities of autocoid release, which temporarily suppresses sensitization and discomfort. Any form of reaction to external mechanical stimulation may identify sensitive patients.

C. Botulinum Toxin.

Treatment of headache and facial pain associated with recurrent or chronic sinusitis according to the methods of the present invention may be practiced by administering botulinum toxin at a biologic activity dose ranging from 0.25-50,000 mouse $LD_{50}$ units. Although one of ordinary skill evaluates dosing of the botulinum toxin based on several factors, including patient-specific factors, the proper dosing, depending on the composition and botulinum toxin immunotype, may be determined by using a regional denervation bioassay.

The methods of the present invention may be practiced with any one or more botulinum toxin immunotypes. The present invention also contemplates the use of compositions comprising botulinum toxin and sequestration agents such as albumin which are disclosed in U.S. patent application Ser. No.: 10/740,755, filed on Dec. 22, 2003, which is incorporated herein by reference, in its entirety.

EXAMPLES

The following Example serves to further illustrate the present invention and is not to be construed as limiting its scope in any way.

Example 1

Patient AA is identified as having myofacial-pain syndrome with chronic pain along the cervical spine. The clinician considers oral therapy with tricyclic antidepressant drugs, with common and sometimes unwanted side effects often used to treat myofascial pain, versus recommending more invasive and more expensive botulinum toxin injections. The clinician elicits evidence of a past history of atopic allergy in the form of recurrent allergic rhinitis. The clinician recommends the use of botulinum toxin over oral medication based on the atopic-disease association to beneficial results.

Example 2

A clinician conducting a clinical study with double-blinded parallel control groups constructs inclusion criteria. The clinician chooses the presence of atopic disease in one of the study groups in order to increase the probability of showing a statistical difference with respect to the control groups. The clinician would be targeting primary-headache disorders to include tension, cluster, migraine, post operative wound pain, myofascial pain or secondary headache syndromes.

Example 3

A clinician conducting a clinical study with double-blinded parallel control groups, constructs inclusion criteria. The clinician selects the presence of effective antagonistic gestures or tactile suppression, referred to as geste antagonists phenomenon, as entry criterion to one of the study groups in order to increase the probability of showing a statistical difference with respect to the control groups. The clinician would be targeting primary-headache disorders to include tension, cluster, migraine, post-operative wound pain, myofascial pain or secondary-headache syndromes.

Example 4

A case study was conducted on a population of subjects for which botulinum toxin was used primarily for the treatment of myofascial pain, post sinusitis pain, trigeminal neuralgia, or pain associated with a chronic post operative wound incision temporally remote from the surgical procedure. Patients where questioned as to the presence of concomitant diseases, age, duration of disease, presence of surgical procedures, radiologic findings, sex, and antagonistic and beneficial behaviors. A concordance analysis was performed with the presence of concomitant disease parameters and relationship to botulinum toxin effectiveness. Chi square analysis was performed for statistical validation. Based on analysis of pain response to botulinum toxin administration, analysis of pain attributes, concomitant disease states, and physical signs, concordance analysis was performed to identify features and patient characteristics which would predict therapeutic outcome of botulinum toxin administration. The study group initially involved 51 patients with trigeminal neuralgia, myofascial pain, chronic postoperative wound pain, muscle tension headache, temporal mandibular joint syndrome with bruxism, and atypical facial pain. The response to each diagnostic category is listed in Table 1. Chronic pain associated with post-dental extraction was least responsive and differed from other forms of post operative wound pain. Other forms of post operative wound pain occurred after sinus surgery, acoustic neuroma surgery, parotidectomy, orbital enucleation, orbital and eye surgery, craniotomy, temporal mandibular joint surgery, and cervical exploration and reconstruction for removal of neoplasm and cancer. Based on diagnostic criterion alone, post dental extraction wound pain was thought to be poorly responsive to botulinum toxin ($p<0.05$, chi square).

TABLE 1

Treatment of pain syndromes of the head and neck with botulinum toxin.

| Pain Syndrome | Response Ratio | % Responsive Subjects |
|---|---|---|
| Trigeminal neuralgia | 19/27 | 70.4 |
| Post-operative wound pain | 25/32 | 78.1 |
| Myofacial headache | 28/36 | 77.8 |
| TMD | 6/8 | 75.0 |
| Post-dental extraction | 2/7 | 28.6 |

Overall % Responsive Subjects = 73%.

Example 5

Within the study population, efforts to characterize patients with increased responsiveness to botulinum toxin treatment initially involved retrospective review of disease characteristics and associative medical disease states followed by prospective analysis. Two associative medical disease states were: 1) presence of atopic disease (added because retrospective analysis suggested atopic disease states were noted to be associated with myofascial pain and botulinum was noted to suppress cholinergic urticaria)(see below); and 2) remote migraine history, either common migraine or migraine with aura, (added because of reported case histories of success for the treatment of this disease with this medication). Patients with acute recurrent migraine were excluded from the study, because the initial purpose of the study was to deal with non-migraine forms of head and neck pain, although a portion of patient treated in the study did suffer from concomitant migraine during the course of the study. Other characteristics included history of prior incisional surgery, duration of disease, sex, and age. Physical characteristics evaluated included geste antagonists, which is the phenomenon of pain relief by tactile-sensory stimulation of a site proximal to the anatomic pain region. Other syndromes relieved by tactile stimulation include adult onset spasmodic torticollis, essential blepharospasm, essential head tremors, and bruxism.

With respect to diagnostic categories, no differences in response were noted among the post operative pain, myofascial pain, trigeminal neuralgia, and tension headache groups. No statistically-significant differences were noted with respect to age, sex, or duration of disease. In interviews with patients for atopic-disease predisposition, it was found that 37.2% of the initial-combined sample had symptoms of asthma or eczema, tactile urticaria, or allergic rhinitis with seasonal hayfever. Within this sampling, 17/19 (87%) with head and neck pain and atopic predisposition received benefit with respect to pain after botulinum administration. Only 56% of patients without atopic predisposition experienced relief of pain after botulinum toxin administration.

With respect to selecting patients by tactile relief (geste antagoniste), 80.6% of patients demonstrating this phenomenon benefited from the injections, whereas only 48% of patients not demonstrating the phenomenon benefited. (see Table 2). The difference in response rate was significant using chi square.

TABLE 2

Association of atopic history and geste antagoniste phenomenon with responsiveness to treatment with botulinum toxin.

| Patient | Response Rate | % Responsive Patients |
|---|---|---|
| History of Atopic Disease | 17/19 | 87 ($p < 0.02$) |
| No History of Atopic Disease | 18/32 | 56 |
| Geste Antagoniste | 25/31 | 80.6 ($p < 0.05$) |
| No Geste Antagoniste | 11/21 | 48 |

Example 6

A past history of migraine had no predictive value in an extended study of patients treated with non-migraine-related facial and head pain (Table 3). In this extended study group, the incidence of migraine headache in the remote past approached the frequency in the general population.

TABLE 3

Incidence of migraine in past history of patients with non-migraine facial pain treated with botulinum toxin.

| Patient | Response Rate | % Responsive Patients |
|---|---|---|
| History of Migraine | 19/24 | 79.2 |
| No History of Migraine | 53/72 | 73.6 |
| Incidence of Migraine | 24/93 | 25.8 |

Example 7

The incidence of atopic disease within each diagnostic category is provided in Table 4. With respect to the general population, which exhibits an incidence of atopic disease of about 20-25%, only myofascial pain is significantly associated with increased responsiveness to botulinum toxin. Furthermore, the incidence of atopic disease in patients afflicted with myofascial pain is significantly higher than in patients with trigeminal neuralgia ($P<0.02$, chi sq). Although not reaching statistical significance, the trend for post operative wound pain group was a higher rate of atopy (44.4%). From data analysis, atopic disease appears most commonly in myofascial pain patients. A background medical history of atopic disease is a significant predictor of a beneficial botulinum injection outcome for patients with myofascial pain and chronic post operative wound pain, but not for trigeminal neuralgia and other facial neuralgias grouped in this category (see table 5).

TABLE 4

Incidence of atopic disease in patients with non-migraine facial pain in extended study based on diagnostic category.

| Pain Syndrome | Response Ratio | % Responsive Subjects |
|---|---|---|
| Trigeminal neuralgia and other forms of facial neuralgia | 10/37 | 28 |
| Chronic post-operative wound pain | 12/27 | 44 |
| Myofacial headache | 26/51 | 52 ($p < 0.02$) |

Example 8

With respect to myofascial pain, bruxism and temporal mandibular joint syndrome, trigeminal neuralgia, and chronic post operative wound pain temporally remote from the surgical procedure, no statistically significant concordance could be found with respect to increased responsiveness of botulinum toxin when age, duration of disease, sex, history of surgical procedures, and past history of migraine headache within the diagnostic-specific groups, in the extended prospective analysis. (see Table 5). History of atopic disease and antagonistic gestures specifically did not prove useful in predicting outcomes for trigeminal neuralgia.

TABLE 5

Background history of atopic disease as a predictor of pain response to botulinum toxin administration (extended study with prospective analysis).

| Pain Syndrome | Response Ratio: Atopic | Responsive Ratio: Non-Atopic |
|---|---|---|
| Myofacial headache | 24/40 | 2/11 ($p < 0.01$) |
| Chronic Post-operative wound pain | 12/22 | 0/5 ($p < 0.05$) |
| Trigeminal neuralgia | 7/28 | 4/9 |

I claim:

1. A method comprising the steps of:
   (a) identifying a subject with a pain syndrome and a medical history of one or more atopic diseases;
   (b) selecting a subject of step (a) for the treatment of said pain syndrome with a botulinum toxin; and
   (c) administering a composition comprising a botulinum toxin to said subject, thereby treating said pain syndrome,
   wherein said identification and selection step is made prior to administering botulinum toxin and wherein the pain syndrome is any one or more of the pain syndromes selected from the group consisting of: post-traumatic headaches, cluster headaches, fibromyalgia, cervical radiculopathy, and whiplash.

2. The method of claim 1 wherein said atopic disease is selected from the group consisting of: recurrent hayfever, recurrent eczema and asthma.

3. The method of claim 1 wherein the botulinum toxin is any form of immunotypes A, B, C, D, E, F, or G.

4. A method comprising the steps of:
   (a) identifying a subject with a pain syndrome that exhibits geste antagoniste phenomenon;
   (b) selecting a subject of step (a) for the treatment of said pain syndrome with a botulinum toxin; and
   (c) administering a composition comprising a botulinum toxin to said subject, thereby treating said pain syndrome,
   wherein said identification and selection step is made prior to administering botulinum toxin and wherein the pain syndrome is any one or more of the pain syndromes selected from the group consisting of: post-traumatic headaches, cluster headaches, fibromyalgia, cervical radiculopathy, and whiplash.

5. The method of claim 4 wherein the botulinum toxin is any form of immunotypes A, B, C, D, F, F, or G.

6. The method of claim 1 wherein said composition is administered to the head or neck.

7. The method of claim 4 wherein said composition is administered to the head or neck.

8. A method comprising the steps of:
   (a) identifying a subject with a pain syndrome and an atopic predisposition or a presence of atopic disease;
   (b) selecting a subject of step (a) for the treatment of said pain syndrome with a botulinum toxin; and
   (c) administering a composition comprising a botulinum toxin to said subject, thereby treating said pain syndrome,
   wherein said identification and selection step is made prior to administering botulinum toxin and wherein the pain syndrome is any one or more of the pain syndromes selected from the group consisting of: post-traumatic headaches, cluster headaches, fibromyalgia, cervical radiculopathy, and whiplash.

9. The method of claim 8 wherein the subject identified in step (a) has atopic predisposition.

10. The method of claim 8 wherein the subject identified in step (a) has the presence of atopic disease.

* * * * *